United States Patent [19]

Hewitt

[11] 4,010,252

[45] Mar. 1, 1977

[54] ANTIMICROBIAL COMPOSITIONS

[75] Inventor: Gordon Trent Hewitt, Upper Montclair, N.J.

[73] Assignee: Colgate-Palmolive Company, New York, N.Y.

[22] Filed: Dec. 19, 1974

[21] Appl. No.: 534,270

[52] U.S. Cl. .................................. 424/47; 424/66; 424/67; 424/68; 424/263; 424/324; 424/340; 424/347; 424/353

[51] Int. Cl.² ...................... A61K 7/34; A61K 7/36; A61K 7/38

[58] Field of Search ....................... 424/329, 47, 68

[56] References Cited

UNITED STATES PATENTS

| | | | |
|---|---|---|---|
| 2,328,690 | 9/1943 | Steele | 424/76 |
| 2,546,791 | 3/1951 | Slifkin et al. | 424/76 X |
| 2,586,287 | 2/1952 | Apperson et al. | 424/68 |
| 2,586,288 | 2/1952 | Apperson et al. | 424/68 |
| 2,703,332 | 3/1955 | Bindler et al. | 424/233 X |
| 3,014,236 | 6/1962 | Stecker | 424/27 |
| 3,014,844 | 12/1961 | Thiel et al. | 424/46 |
| 3,093,546 | 6/1963 | Atkinson | 424/76 X |
| 3,152,039 | 10/1964 | Mattson | 424/76 X |
| 3,244,585 | 4/1966 | Stecker | 424/231 |
| 3,288,681 | 11/1966 | Goldberg et al. | 424/47 X |
| 3,326,808 | 6/1967 | Noseworthy | 424/231 X |
| 3,506,761 | 4/1970 | Rubino | 424/231 X |
| 3,577,539 | 5/1971 | Vinson | 424/231 |
| 3,751,565 | 8/1973 | Santorelli | 424/231 X |
| 3,792,068 | 2/1974 | Luedders et al. | 424/47 |
| 3,830,913 | 8/1974 | Harich | 424/329 X |

FOREIGN PATENTS OR APPLICATIONS

| | | | |
|---|---|---|---|
| 484,048 | 6/1952 | Canada | 424/329 |
| 1,130,405 | 9/1956 | France | 424/329 |
| 11,619 | 2/1956 | Germany | 424/329 |
| 1,928,192 | 6/1969 | Germany | 424/329 |
| 508,341 | 7/1971 | Switzerland | 424/329 |
| 1,239,641 | 7/1971 | United Kingdom | 424/329 |
| 656,747 | 8/1951 | United Kingdom | 424/329 |
| 743,408 | 1/1956 | United Kingdom | 424/329 |

OTHER PUBLICATIONS

Walter, et al., Journal of Pharmaceutical Sciences, 1962, vol. 51, pp. 770–772.

*Primary Examiner*—Dale R. Ore
*Attorney, Agent, or Firm*—Steven J. Baron; Norman Blumenkopf; Herbert S. Sylvester

[57] ABSTRACT

There is disclosed antimicrobial compositions based upon the combination of an antimicrobially effective poly (quaternary ammonium) compound and an antimicrobially effective simple anionic component. There is also disclosed methods of making the same and products made therefrom.

14 Claims, No Drawings

ANTIMICROBIAL COMPOSITIONS

This invention relates to new compositions having antimicrobial properties, methods of making the same and products employing the compositions. More particularly the invention relates to the composition resulting from the combination of a poly (quaternary ammonium) compound having antimicrobial properties and simple anionic component having antimicrobial properties. The invention finds particular utility in the area of personal hygiene.

The prior art teaches that certain polymeric quaternary ammonium compounds are by themselves useful as bactericides and the like. The art also teaches that simple quaternary materials may be combined with poly (anionic) materials such as certain polymers which are operative to aid in the deposition and retention of the quaternary members on a substrate. One may also find teachings in the art of combining a cation of which the quaternary ammonium compound may be representative, with an anion such as an antimicrobial agent. Review of the art also reveals that certain members more properly called polysalts are composed of a poly anionic antimicrobial agent in combination with a non-antimicrobial poly (anionic) member. Polyelectrolyte complexes (polysalts) consisting of the interaction product of a non-antimicrobial polyanionic compound with a non-antimicrobial poly cationic compound are also known. One does not, however, find any teachings of the combination of an antimicrobial poly (quaternary) member in combination with an anionic member also having antimicrobial properties. In point of fact, the art specifically contraindicates the combination of these two different classes (viz., different in ionic charge) of antimicrobial agents. The art states that the combination of the foregoing will mutually inactivate each other with the resultant consequence that the combination is ineffective as an antimicrobial agent.

In this regard attention is directed to U.S. Pat. No. 3,108,036 and the classic article in the literature entitled "Antibacterial Activity of Mixtures of Quaternary Ammonium Compounds and Hexachlorophene" by Walter & Gump, appearing in the *Journal of Pharmaceutical Science*, Vol. 51, pgs. 770–772, (August 1962).

It has now surprisingly been found that by the proper selection of the poly (quaternary ammonium) compound and antimicrobially effective anionic compound, there occurs no mutual cancellation as referred to in the art. In fact, certain of the objectionable properties of the anionic antimicrobial compounds are ameliorated or in certain cases eliminated altogether.

The novel compositions of the instant invention being derived from the combination of a cationic material with an anionic material possess the desirable antimicrobial properties of each of the precursor materials. The poly (quaternary ammonium) compounds are broad-spectrum antimicrobial agents, i.e., they are effective against gram-positive bacteria as well as gram-negative bacteria. The anionic antimicrobial agents are effective against gram-positive bacteria and certain gram-negative bacteria.

Gram-negative organisms are potential contaminants of the skin and other surfaces upon which anti-bacterial usage has been found desirable and it is therefore essential to reduce the population of these organisms as well as gram-positive organisms to obtain the maximum beneficial effect.

Certain gram-negative organisms, particularly of the enteric type and the resistant Pseudomonads, are not particularly sensitive to the usual agents employed in degerming the skin. Though not generally resident flora on normal skin, it is undesirable to permit their proliferation in the environment. Many antibacterial agents which have been used, while having in certain instances some effect on gram-negative organisms, require either an irritatingly high concentration or too long an exposure time. The foregoing often results in an undesirable percutaneous absorption of the antibacterial material. This is of considerable importance with respect to the long term effects of traces of these materials which may accumulate in the body. It is therefore desirable to provide for an antibacterially effective material that is slowly released such that it has less chance of entering the body at such initial levels as to make its detoxification and elimination a problem.

The elimination of human body odor has long been an objective in the field of proprietary medicine. The prevailing theories on the causes of human body odor are based on the underlying assumption that body odor is caused by secretions from the apocrine glands. Perspiration or secretion from the eccrine glands, on the other hand, assist in the regulation of body temperatures by dispelling heat through evaporation of moisture from the surface of the skin. perspiration also functions in other capacities such as by eliminating lactic acid which is formed during muscular exercise and by protecting the skin from dryness.

Some individuals secrete sweat that has an offensive odor (bromoidrosis) and in certain cases it is colored (chromidrosis). In other cases, individuals perspire freely even during the winter months. This condition is known as hyperidrosis. In the majority of cases, however, perspiration is not due to a biological malfunction but is a normal body function.

An important factor of concern regarding perspiration is the offensiveness of the odor thereof. These appocrine secretions do not of themselves normally have an objectional odor. Degradation of the components of sweat both by chemical and microbial attack creates the unpleasant odor that is sometimes associated with skin secretions. In addition to odor, the normal course of perspiration often results in the formation of wet spots on adjacent clothing, especially in the area of the axillae. This is especially annoying to many people. It is therefore desirable to reduce perspiration as well as to control the resulting odor. Thus, if perspiration is minimized, the formation of odor is inhibited. Accordingly, there are currently available "deodorants" which, in effect are antiperspirants. These products usually embody aluminum compounds and are generally applied to the axillary regions of the body. The aluminum compounds act as astringents and thereby reduce perspiration in the regions where applied. These have been and still may be used in the form of dust-on powders, ointments, liquid roll-ons, liquid sprays, pastes and more recently, aerosol compositions.

A more sophisticated approach to the problem has taken the form of embodying bacteriostats in compositions intended for use on the body. Skin-substantive bacteriostats are chosen so that the bacteriostat remains on the surface of the body for a period of time subsequent to the use thereof. This type of product has been developed because of the theory that body odor is not due simply to the presence of the perspiration, but rather that body odor is caused by bacterial on the skin which break down the perspiration and natural body oils into odoriferous products. Thus, the presence of a bacteriostat on the skin is expected to reduce the multiplication and growth of bacteria and thereby inhibit the undesirable action of the bacteria on the perspiration.

One aspect of the invention accordingly contemplates the use of an antimicrobial composotion in both non-astringent deodorants as well as in antiperspirant-/deodorant compositions.

A review of the deodorant literature indicates that there has been a continuing trend toward the so called dry products.

With the advent of pressurized aerosol dispensers, aerosol sprays have become extremely popular. Many aluminum salts are soluble in water but are insoluble in organic solvents such as alcohols and the commonly used propellants. Various aluminum complexes were developed which had greater solubility in organic solvents and, therefore, lent themselves to use in liquid aerosol compositions. Initially, the aerosol antiperspirants were so-called wet sprays which utilized water, or other solvent for the astringent salt in the composition, along with a common propellant.

Dry aerosol spray compositions were thereafter developed. These utilized powdered aluminum complexes, or other well-known antiperspirants or astringents along with a propellant.

Some of these compositions have been further modified by the addition of a relatively large amount of a non-volatile emollient. Such vehicles have usually been lipophilic materials which exhibit very little water solubility. These sometimes insulate the active antiperspirant from contact with moisture on the skin and thereby delay the onset of astringent action.

To promote dissolving of the chlorhydrate (or other active material) and any hydration and hydrolysis that results, water soluble vehicles may be employed.

Various of the prior art deodorant and antiperspirant compositions have been reported by some to have drawbacks such as separation of the composition upon aging, caking of the composition, valve clogging, dripping of the spray upon application, and corrosive action of the soluble salt. With respect to those drawbacks, one embodiment of this invention is directed. That embodiment contemplates an improved product which has improved properties and the advantages of good feel, non-stickiness, good suspension, low staining, the valve remains clear, and the composition does not drip. This is accomplished by providing a composition containing an active astringent powder, a relatively low vehicle content, an adequate suspending agent, and a propellant.

It is accordingly an object of this invention to provide for a new composition of matter derived from the combination of an antimicrobial cationic poly (quaternary ammonium) compound and an antimicrobial anionic compound.

It is another object of this invention to provide an improved composition for inhibiting body odor.

It is yet another object of the present invention to provide these compositions which have the advantage of not causing any appreciable skin irritation so that the same can be used for purposes where they come into contact with the skin.

It is still a further object to avoid one or more drawbacks of the prior art.

These and other objects of the invention will become more apparent from the following detailed description and claims.

The aforesaid composition is believed to be both a polymer and an electrolyte and as such has the following properties: moderately high molecular weight; lipid insolubility; water insolubility; reversible hydratabilty; alcohol and glycol solubility; and a nearly neutral pH.

It has been found that the compositions of the instant invention exhibit greater antimicrobial effectiveness than exhibited by either of the two components alone.

The composition of the invention when topically applied to the skin shows a lower constant level of adsorption of the anionic component into the blood than does the anionic antimicrobial agent alone. In other words, the free anionic antimicrobial agent when topically applied has in certain instances been found to migrate quickly into the blood stream, thereby leaving the site of application in a short time, ergo, the benefits thereof being of short duration. Contrarywise, topical application of the instant composition provides for a slow steady release of the antimicrobial agent in relatively low, but, nevertheless, antimicrobially inhibiting quantities.

It is accordingly the foregoing desirable property of the instant invention which renders the same eminently suitable for formulation into various products useful in the area of personal hygiene, i.e., deodorants and the like.

The anionic antimicrobial agents operative herein fall into several classes as will be further detailed hereinafter. They are:
1. diphenyl ethers, such as the polyhalogenated hydroxy diphenyl ethers, more specifically those containing multiple halogen substituents, such as triclosan and the like.
2. simple phenolics, such as phenol, cresol, o-phenylphenol, 4-hexylresorcinol; and the halogenated phenolics, such as p-chlorometa-xylenol, dichlorometa-xylenol, o-benzyl p-chlorophenol and p-isoamylphenol.
3. Bis-phenolics, e.g.
   2,2'-methylene bis (3,4,6-trichlorophenol),
   2,2'-methylene bis (4,6-dichlorophenol),
   2,2'-methylene bis (4-chlorophenol),
   2,2'-thio bis (4,6-dichlorophenol).
4. Salicylanilides, e.g.
   salicylanilide,
   monohalogenated salicylanilide,
   polyhalogenated salicylanilide.

More specifically the instant invention contemplates the use of the following anionic antimicrobial agents, though the invention is not limited to those disclosed herein.

The diphenyl ethers have the general formula

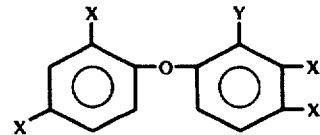

wherein Y is hydrogen or hydroxy and X halogen such as Cl-, Br-, or CF$_3$ or -H; preferably chlorine wherein Y is hydroxy, such as those disclosed in U.S. Pat. No. 3,800,048, the entire disclosure of which is incorporated herein be reference.

Halophenols suitable for the practice of this invention are halogenated monohydric phenols and embrace halogenated parasiticidal phenols including alkyl and phenyl substituted phenols which have been chlorinated or brominated. Halophenols of this invention are those defined by the structure

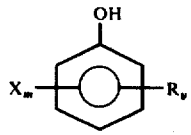

wherein R is a substituent selected from the group consisting of methyl and phenyl, each X is at least one of bromine and chlorine, y is 0 or 1, and m is an integer of about 1 to 5 (5−y), inclusive. Suitable halophenols are those having mixed chlorine and bromine as well as those having a single halogen species and include 2-bromo-4-chlorophenol, 2-bromo-4,6-dichlorophenol, 2,6-dibromo-4-chlorophenol, 2-chloro-4-phenylphenol, 2,3,4-trichlorophenol, 2,3,6-trichlorophenol, 2,4,5-trichlorophenol, 4-bromophenol, 2-bromophenol, 2,4-dibromophenol, 4-chloro-m-cresol, 2-chloro-4,6-dibromophenol, pentachlorophenol, pentabromophenol, 2,3,5,6-tetrachlorophenol, 2,3,4,5-tetrachlorophenol, 2,3,4,6-tetrachlorophenol, 2,3,5,6-tetrachloro-p-cresol, 2,4,5,6-tetrabromo-m-cresol, 2,4,6-trichlorophenol, 3,4-dichlorophenol, 2,3-dichlorophenol, 2,5-dichlorophenol, 2,6-dichlorophenol, 2,4-dichlorophenol, 2,3,6-tribromo-p-cresol, 2,4,6-tri-chloro-m-cresol, 2,4,6-tribromo-m-cresol, 4-chlorophenol, 3-chlorophenol, 2-chlorophenol, 4,6-dibromo-o-cresol, 2,5-dibromo-p-cresol, 3,6-dibromo-2-chloro-p-cresol, 2-bromo-4-phenylphenol, 4-bromo-2-phenylphenol and 4-chloro-2-phenylphenol and the like.

The (unalkylated) halogenated bis-phenol used in accordance with the present invention can be represented by the following structural formula:

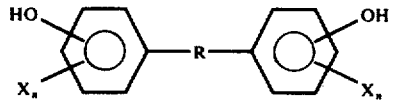

wherein X represents a halogen such as chlorine or bromine, n represents an integer of about 1 to 3, and R represents -S- or a divalent alkylene radical having 1 to 4 carbon atoms such as —CH$_2$—, —CH$_2$CH$_2$—, —CH(CH$_3$)—, —C(CH$_3$)$_2$—, —CH$_2$CH$_2$CH$_2$— and the like. The preferred compounds are symmetrical in structural configuration.

Specific examples of the unalkylated halogenated bisphenols include 2,2′-dihydroxy halogenated diphenyl methanes such as 2,2′-dihydroxy-3,5,6,3′,5′,6′-hexachlorophenyl methane (hexachlorophene), 2,2′-dihydroxy-3,5,3′,5′-tetrachlorodiphenyl 2,2′-dihydroxy-4,5,4′,5′-tetrachlorodiphenyl methane, and 2,2′-dihydroxy-5,5′-dibromodiphenyl methane, 2,2′-dihydroxy-3,5,3′,5′-tetrachlorodiphenyl sulfide and 2,2′-dihydroxy-5,5′-dichlorodiphenyl sulfide and the like.

The alkylated halogenated bis-phenols used in conjunction with the unalkylated halogenated bis-phenols in the present invention can be any suitable bis-phenol composition characterized by the presence of short-chain alkyl groups in the aromatic rings. These substances can be represented according to their chemical structure as follows:

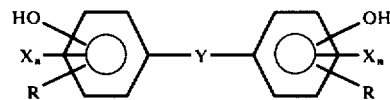

wherein X represents a halogen such as chlorine or bromine, n is an integer of about 1 to 3, R is an alkyl group containing about 1 to 4 carbon atoms and Y is a divalent radical including alkylene radicals having about 1 to 4 carbon atoms such as —CH$_2$—, —CH$_2$CH$_2$—, —CH(CH$_3$)—, C(CH$_3$)$_2$—, —CH$_2$CH$_2$CH$_2$—, etc,; halo-substituted alkylene radicals having 1 to 4 carbon atoms such as —CHCl—, —CHBr—, —CHClCHCl—, —CH(CCl$_3$)—, —CH(CBr$_3$)—, etc.; and -S-. The preferred compounds are symmetrical in structural configuration. Specific examples of the alkylated halogenated bis-phenols include
2,2′-dihydroxy-3,3′-dimethyl-5,5′-dichlorodiphenyl sulfide,
2,2′-dihydroxy-3,3′-dimethyl-5,5′-dichlorodiphenyl trichloroethane,
2,2′-methylene-bis(4-chloro-6-isopropyl-phenol),
2,2′-methylene-bis(6-sec-butyl-4-chlorophenol),
2,2′-ethylidene-bis(4-chloro-6-isopropylphenol),
2,2′-ethylidene-bis(6-sec-butyl-4-chlorophenol),
2,2′-isopropylidene-bis(4-chloro-6-isopropylphenol),
2,2′-isopropylidene-bis(6-sec-butyl-4-chlorophenol)
and the like.

A convenient generic formula to represent both the diphenyl ethers and the bis-phenols is the following:

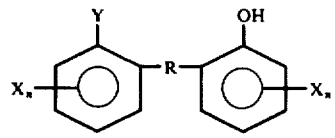

wherein R is —CH$_2$, S or O, X is halogen, n = 1–3 and Y is H or —OH.

The halogenated salicylanilides which find utility in this invention conform to the general structural formula:

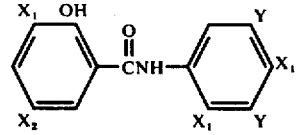

wherein each X$_1$ represents hydrogen or halogen, X$_2$ represents a halogen, and Y represents hydrogen, halogen or trifluoromethyl.

The preferred halogenated salicylanilides which are encompassed by the above general formula include 3,5,4′-tribromo-salicylanilides, 5-bromosalicyl-3,5-di(-trifluoromethyl) anilide, 5-chlorosalicyl-3,5(trifluoromethyl) anilide, 3,5- dichlorosalicyl-3,4-dichloroanilide and 5-chlorosalicyl-3-trifluoromethyl-4-chloroanilide and the like. Other halogenated salicylanilides which come within the above general formula are disclosed in U.S. Pat. No. 2,703,332, which also discloses a method for their preparation.

The (polyhalo-salicylanilides) used in the present invention can be any suitable salicylanilide composition characterized by the presence of halogen atoms in both of the aromatic rings. These compounds can be represented according to their chemical structure as follows:

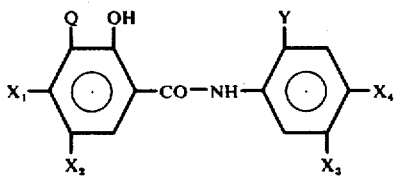

wherein Q represents a member selected from the group consisting of hydrogen, chlorine, bromine, and iodine, $X_1$ and $X_2$ each represent a member selected from the group consisting of hydrogen, chlorine, bromine, iodine and $CH_3$, $X_3$ represents a member selected from the group consisting of hydrogen, chlorine, bromine and $CH_3$ and $X_4$ and Y each represent a member selected from the group consisting of hydrogen, chlorine and bromine, there being at least two halogen substituents in the X positions. Specific examples of compounds coming within the aforementioned general formula include 5-chlorosalicylic acid-3',4'-dichlorosalicyclic acid-3',4'-dichloroanilide, 4,5'-dichlorosalicylic acid-2',3',4'-trichloroanilide, and 3,5-trichlorosalicylic acid-2',3',4'-trichloroanilide and the like. These compositions compositions are produced, generally, by the reaction between a halogenated salicylic acid and a halo-substituted aniline.

Within the above group there may also be employed 3,5,4'-trihalosalicylanilides and the 5,4'-dihalosalicylanilides which have the following general formula:

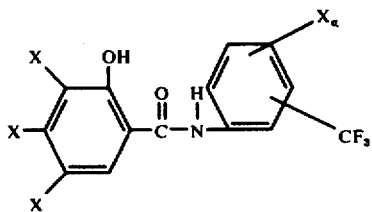

In the above formula X is chlorine, bromine or iodine and n is 0–1. As will be apparent, when n is O, the above formula represents the 5,4'-dihalosalicylanilide; when n is 1, the 3,5,4'-trihalosalicylanilides are represented.

The trifluoromethyl halogenated salicylanilides usable in the formulation of the present invention have the following general formula:

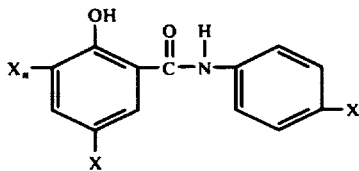

In the foregoing formula, X is chlorine, bromine, iodine or hydrogen and a is 0–2. In this formula, there must be at least one and not more than three directly attached halogen atoms, none of which is adjacent to any of the others or to the $CF_3$ group. These materials are described more completely in U.S. Pat. Nos. 3,041,236 and 3,244,585. Examples of these trifluoromethyl salicylanilides are 3,5-dibromo-3'-trifluoromethylsalicylanilide; 5-chloro-3'-trifluoromethylsalicylanilide; 5-iodo-3'-trifluoromethylsalicylanilide; 3,5-dichloro-3'-trifluoromethylsalicylanilide; 5-chloro-3'-trifluoromethylchlorosalicylanilide; 3,5,4'-tribromosalicylanilide; 3,5,4'-triodosalicylanilide; 3,5,4'-trichlorosalicylanilide; 3,5-dibromo-4'-chlorosalicylanilide; and the like. Examples of the dihalosalicylanilides usable in synergistic admixture with the trihalosalicylanilides are 5,4'-dichlorosalicylanilide; 5-chloro-4'-bromosalicylanilide; 5-bromo-4'-chlorosalicylanilide; 5-iodo-4'-bromosalicylanilide; and the like.

While as a general practice the anionic antimicrobial compound will be used singly, it may, however, be used in combination with one or more of the other available anionic antimicrobial components referred to earlier. In the latter instance, the ratio of one to the other may vary over a wide range providing the other parameters of the invention are met, such as total amount of anionic material relative to poly (quat), etc.; as will be further detailed.

The poly (quaternary ammonium) compounds useful in the instant invention include those having the following general formula

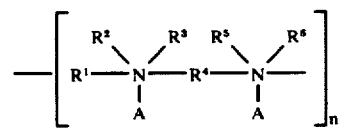

wherein n is an integer representing the number of multiple recurring units in the polymeric chain, such as about 100–200, A is the anion of an acid, and $R^1$, $R^2$, $R^3$, $R^4$, $R^5$ and $R^6$ are all hydrocarbon radicals joined to the nitrogen by carbon. $R^1$ and $R^4$ being polymethylene, $R^2$, $R^3$, $R^5$, $R^6$ being alkyl. In one preferred embodiment the several R's are so selected in relation to each other than $R^1$ contains a singly-bonded carbon adjacent to the nitrogen and of the remaining radicals no two attached to one nitrogen contain a multiple bonded carbon adjacent to the nitrogen. $R^2$ and $R^3$ can be externally joined to form a ring, as can $R^5$ and $R^6$.

$R^1$ is about $C_6$ to $_{20}$, preferably about 10 to 16;
$R^2$ is about $C_1$ to $_3$, preferably about $C_1$;
$R^3$ is about $C_1$ to $_3$, preferably about $C_1$;
$R^4$ is about $C_6$ to $_{20}$, preferably about 10 to 16;
$R^5$ is about $C_1$ to $_3$, preferably about $C_1$;
$R^6$ is about $C_1$ to $_3$, preferably about $C_1$.

$R^2$, $R^3$, $R^5$ and $R^6$ may have hydroxy substitution for one hydrogen.

Also included are those having the formula:

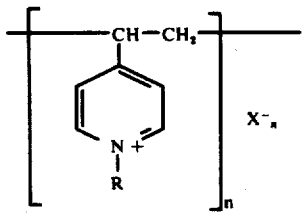

wherein $n = 10^2$ to $5 \times 10^3$, R is an alkyl group of about $C_{6-15}$, preferably about 8–10;
X is a halide or metho or etho sulfate; referred to as a poly (N-alkyl vinyl pyridinium) salt.

A specific subgeneric group falling within the first mentioned formula, would be the ionenes, which have the formula

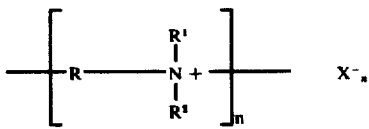

wherein R is a normal or branched chain alkylene group having about 6 to 16 carbons; $R^1$ and $R^2$ is $CH_3$, $-C_2H_5$, or $-C_2H_4OH$; $n =$ about 4 to 200; and $X^- =$ $F^-$, $Cl^-$, $Br^-$, $I^-$, $(OSO_3CH_3)^-$, or $CH_3COO^-$.

A preferred poly(quaternary ammonium) compound of the foregoing type is, for example, one wherein R is $(CH_2)_{10}$, $R^1$ and $R^2$ are each $CH_3$, and X is Br, i.e., having repeating units of the formula:

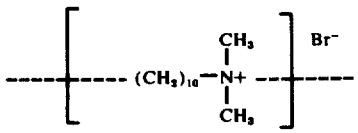

The poly (quaternary ammonium) compound will generally have a molecular weight of about 5,000 to 40,000, preferably about 15,000 to 35,000. The proportions are about one mole of anionic component to about one equivalent of polycationic. Thus, the molecular weight of the latter does not effect the weight ratios.

In preparing the novel compositions of the instant invention one may initially form an aqueous solution of the anionic antimicrobial agent, which component is in the preferred embodiment relatively water soluble. An aqueous solution of a salt of the weakly acidic anionic antimicrobial agent in which form it has increased solubility in water and hydroalcoholic solvent systems in therefore most desirable. Thereafter, the solution may be added to the poly (quaternary ammonium) compound in either solid or solution form, or, the latter may be added to the solution of the anionic. It is preferred practice in most instances to employ an alkaline solution of the anionic. The pH thereof may vary from about 9.5 to 11, preferably about 10.2 to 10.8 with adjustment accomplished by base in accordance with the art. The aforesaid combination if prepared in an aqueous system will generally produce a somewhat gummy or viscous mass which is preferably dried and then re-dissolved in a suitable solvent, such as a $C_{1-6}$ lower alkanol, e.g., methanol, ethanol, propanol, etc. Most suitable apparatus for carrying out such simple mixing operations are operative herein. Having thus made the instant composition (at temperatures of about ambient to about 50° C, the same may thereafter be employed for a variety of end uses.

The compositions of the instant invention can be in solution (which requires a relatively high proportion of alcohol or solvent) or it can be used as a fine emulsion which may be prepared if a solution thereof is suitably poured into water with adequate stirring; prepared in this manner, the compositions of the invention may be suitably employed in emulsion or cream forms.

An alternative method of preparation of the compositions of the instant invention is to mix the anionic antimicrobial agent in its non-salt, i.e., weak acid state with the poly cationic material in its free quaternary ammonium base form. In effect this would represent the neutralization of a weak acid with a strong polybase. It would best be carried out in a suitable water solvent mixture and could be guided by observations in the pH of the mixture.

In compositions containing an aqueous medium, the solvent can be water or an aqueous alcoholic solution. It may contain varying amounts of a water-soluble or miscible saturated lower aliphatic alcohol such as ethanol isopropanol, propylene glycol or the like, if desired. In a liquid product, it is preferred to employ a minor proportion of an alcohol, preferably ethanol, in an amount from about 5 to 30% by weight of the composition to aid in fast drying of the product after application and in the solubilization of certain materials such as water-insoluble perfume and the like. It will be understood that the water and alcohol and any other ingredients in the solvent medium should be proportioned so as to form a homogeneous or uniform solvent medium effective to dissolve or solubilize the materials, including the instant active ingredient.

In general, the mixture containing the materials, may be prepared in any suitable form. It is preferred to utilize it in the form of a liquid (including clear solutions and emulsion types). Such liquid may be adapted for various methods of application. It may be dispensed or applied by means of a roll-on applicator, by spraying from a squeeze bottle, by use of propellant gas from a valved container commonly known as an aerosol type or by use of fingers or an instrument. The viscosity of the liquid will be adjusted so as to achieve the desired flow for the particular means of dispensation.

Thus, it is desirable in certain instances to incorporate a gum or gum-like material in order to have a more viscous flow. Gums which are in themselves ionic (i.e., polycarboxylic acids, polysulfonates) should be avoided as thickeners. For example, liquid compositions designed for application by use of a roll-on apparatus must flow from a reservoir to a passage between the ball and the adjacent wall or neck of the container. The viscosity of the liquid should be controlled taking into consideration the clearance of the passage so that the product flows in a smooth manner without dripping or gelling of the product. Many suitable gums such as those known in the art may be employed for this prupose. In general, the amount of thickening agent used, depending upon its thickening power, is within the range of about 0.1 to 2% by weight.

Any suitable surface-active agent may be incorporated in the product also which is compatible in said liquid. It is desirable to include a water-soluble nonionic surface-active agent in the composition. Such material possesses dispersing or solubilizing properties in the solvent medium, e.g., solubilization of insoluble perfumes, and contributes increased wetting characteristics. It is employed in a minor amount in the solution which is usually within the range of about ¼ to 2% by weight of the composition.

The preferred surface-active agents contain usually a long-chain aliphatic hydrophobic organic group, e.g., having at least about 5 and usually about 8 to 30 carbon atoms, condensed with an alkylene oxide of about 2-4 carbons in an amount sufficient to render the product water-soluble, and usually within the range of about 5 to 100 alkylene oxide groups. Suitable examples are polyethyleneoxide ethers of an alkyl phenol or a higher aliphatic alcohol. The alkyl phenol ethers usually have about 6 to 15 carbons in the alkyl group and about 5 to 20 moles of ethylene oxide, specific examples of which are Igepal CO-630 and 710. The polyethylene oxide condensates, preferably having about 6 to 30 moles, with a fatty alcohol of 8 to 22 carbons such as lauryl, tridecyl, myristyl, cetyl and stearyl alcohols, may be used also. A typical product is a fatty alcohol of 12 to 14 carbons condensed with about 10 moles of ethylene oxide.

As indicated, various adjuvant materials may be incorporated in the compositions in suitable amounts. Thus, the product will ordinarily contain perfume and coloring material which should be compatible therewith. Minor amounts of materials considered as having an emollient effect, such as glycerine, allantoin, and lanolin derivatives such as a water-soluble acetylated ethoxylated lanolin derivative, may be incorporated therein.

There may be included a suitable ultra-violet absorber in the product, if desired, to inhibit fading of the color of the composition in sunlight. Any suitable ultra-violet absorber compatible and soluble in the liquid medium may be employed. In general, they are substantially invisible when applied to human tissue. It is preferred to employ ultra-violet absorbers having a 2-hydroxy benzophenone group or nucleus, and particularly 2,2'-4,4'-tetrahydroxy benzophenone.

Other materials which may be added include preservative, additional anti-bacterial materials, opacifying agents such as cetyl alcohol or the like in compatible to form an opaque liquid, silicone fluids, etc.

The liquid composition may be admixed with a propellant material and dispensed as an aerosol. Any suitable normally gaseous substance may be employed in known manner such as the liquefied normally gaseous low molecular weight aliphatic hydrocarbons, e.g., mixture of propane and isobutane, and halogenated hydrocarbon propellants known in the art as the Genetrons and Freons which dispense the product in the form of a mist or spray. Other inert propellant materials which dispense the product as a viscous liquid from a valved container rather than as a spray may be employed also, such as nitrogen or the like.

In the manufacture of a cream, suitable fatty material and an emulsifying agent will be combined with the aluminum compound, optionally, an antimicrobial agent and fabric-corrosion inhibitor in water to form an aqueous phase and an oily or fatty phase which are combined in the form of a cream. Suitable fatty and emulsifying materials may be selected from those disclosed in said U.S. Pat. Nos. 2,586,287 and 2,586,288.

In accordance with a further embodiment of the invention there is provided a composition in a pressurized container for the production of a dry spray of an antibacterial composition which comprises an effective amount of the antibacterial composition above referred to, a powdered antiperspirant material in an amount sufficient to have an effective antiperspirant action, a propellant fluid for maintaining pressure in the container and aiding in the discharge of the antiperspirant composition therefrom, a nonvolatile, propellant soluble vehicle in an amount of between about 0.3 and 1.6 percent by weight, and a suspending agent capable of maintaining the powder component of the composition in suspension. The active antiperspirant ingredient employed herein as well as for the other embodiments is any one or more of the known salts having astringent properties such as aluminum, zinc, iron, or zirconium salts or complexes, which salt should also be insoluble in the propellant and vehicle. For example, such compounds include, but are not limited to, zirconium salts such as: zirconium chloride, zirconium oxychloride, zirconyl hydroxychloride, and zirconium sulfate; zinc salts such as: zinc hydroxychloride, zinc hydroxybromide, zinc sulfate, and zinc phosphate; aluminum such as: aluminum basic chloride, aluminum chloride, aluminum bromide, aluminum sulfate, aluminum oxychloride, aluminum oxysulfate, and hydrates of the aluminum salts, such as aluminum chloride hexahydrate, and iron salts such as ferric sulfate and ferrous sulfate. Many inorganic-organic astringent salt complexes and mixtures of astringent salts can also be used as long as they remain insoluble in both alcohol and the propellant.

As used herein, the term "aluminum basic chloride" refers to those compounds having the empirical formula: $Al_2(OH)_{(6-x)} Cl_x$; wherein $x$ is a positive number of from 1 to 5. Similar considerations apply with respect to aluminum basic iodide and aluminum basic bromide.

Particularly useful results are obtained when an aluminum basic chloride having an aluminum to chloride mol ratio of from about 2:5 up to about 2.1 to 1, advantageously between about 1:1 to about 2:1. One desirable salt is actually a mixture of aluminum salts having an apparent atomic ratio of aluminum to chlorine of about 2:1, e.g., an average of about 2.1 to 1.9:1, and an empirical formula of $Al_2(OH)_5Cl$ in aqueous solution.

The active antiperspirant material should be present in the composition as a powder and in an amount of about 0.5 to 15% by weight, preferably an amount of about 1 to 6%.

Another component of the invention is a nonvolatile, propellant soluble vehicle where an aerosol embodiment is contemplated. Examples of such compounds are fatty acid esters, fatty alcohols, hydrocarbons such as mineral oil, lanolin and its derivatives, silicone oils such as dimethyl polysiloxane, diesters of dibasic acids, and nonionic vehicles such as the esters and partial esters of fatty acids containing from 6 to 22 carbon atoms such as those disclosed in U.S. Pat. No. 3,014,844.

Useful vehicles include but are not limited to isopropyl palmitate, isopropyl myristate, butyl stearate, glyceryl trioleate, stearyl palmitate, ethylene glycol, diethylene glycol, triethylene glycol, tetraethylene glycol, trimethylol propane, propylene glycol, 1,4-hexanediol, 1,2,6-hexanetriol, dipropylene glycol, di-n-octyl-n-decyl phthalate, di-n-butyl phthalate, di-n-hexyl phthalate, di-n-octyl phthalate, diethyl sebacate, diisopropyl addipate, dimethyl phthalate, glycerine, ethoxylated lanolin, acetylated lanolin, propylene glycol dipelargonate, 1,3-butanediol, 2-methyl-2-ethyl-1,3-propanediol, ethylene glycol ethyl ether, ethylene glycol methyl ether, diethylene glycol methyl ether, diethylene glycol ethyl ether, 2-methyl-2,4-pentanediol, 1,4-butanediol, 1,2,4-butanediol, diglycerol, oleyl alcohol, cetyl alcohol, lauric alcohol, and mixtures of the above.

Where a non-volatile vehicle is employed in the dry powder embodiment it is in quantities which do not impair the dry powder property of the subject composition. In order to maintain a composition which will deposit a non-greasy, dry-feeling film it is required that this vehicle be used in an amount of not more than about 1.6 percent. This vehicle should be present in an amount of about 0.3–1.6%, preferably, 0.5–1.5%.

Another component of the dry powder embodiment of the invention may include a suspending agent, where desired. The useful suspending agents are finely divided hydrophobically treated clays such as a reaction product of a clay such a bentonite or hectorite with, for example, dimethyldistearyl ammonium chloride. These suspending agents are the hydrophobically treated montmorillonite or hectorite clays available under the trademark Bentone which are prepared by reacting a clay such as bentonite or hectorite in a cation exchange system with a variety of amines. Different amines are reacted to obtain different Bentone suspending agents which may also differ in proportions of $SiO_2$, MgO and $Al_2O_3$. Examples of useful Bentone suspending agents are Bentone-27, which is stearaluminum hectorite, Bentone-34, which is quaternium 18 bentonite, Bentone-38, which is quaternium 18 hectorite, and Bentone-14, which is a clay extended quaternium 18 hectorite, all of which have a particle size of below about 5 microns and are commercially available from the NL Industries, Inc.

The hydrophobic clays where employed should be thoroughly dispersed. Three forms of energy which aid in such dispersion are temperature increase, chemical energy and mechanical shearing action. Chemical energy can be supplied in the form of a polar additive such as alcohol or a high boiling organic liquid such as propylene carbonate. Propylene carbonate, usually in an amount of about 0.05% to about 0.45%, is also particularly helpful when the organic liquid has poor wetting properties, or when dispersion is unusually difficult. As taught by NL Industries in their Data Sheet B-33 of April 1970, high mechanical shearing action is also an important factor. Equipment such as homogenizers, shear pumps, and cooloid mills will give positive results. Examples of useful mixers include, among others, the Cowles Dissolver and the Eppenbach Homogenizer.

The suspending agent if employed is used in amounts of from about 0.1 to about 3%, desirably about 0.1 to 1%, and preferably from about 0.25 to about 0.75% thereof.

The propellant used in connection with various embodiments of the invention may be any non-toxic, liquifiable propellant suitable for use in connection with the dispensing of the material. That is to say, any non-toxic, volatile, organic material which exists as a gas at the temperature of use (and ambient or atmospheric pressure) and which exists as a liquid at the same temperature under superatmospheric pressures can be used as the gas-producing agent. Especially suitable are the $C_3$–$C_4$ aliphatic hydrocarbons, namely liquefied propane, n-butane, and isobuane; halogenated aliphatic hydrocarbons which contain from 1 to 2 carbon atoms and include, by way of example, methylene chloride, Freons such as dichlorodifluoromethane, monochlorodifluoroemethane, dichlorotetrafluoroethane, trichlorofluoromethane, trichlorofluoroethane, difluoroethane, difluoromonochloroethane, trichlorotrifluoroethane, monofluorodichloroethane, pentafluoromonochloroethane; cyclic hexafluorodichlorobutane; octafluoropropane; and cyclic octafluorobutane; and mixtures of two or more thereof. Preferably the saturated hydrocarbons and halogenated saturated aliphatic hydrocarbons are employed in the subject composition. The boiling point of said propellant, or of the mixture of propellants, used in the final product should fall within the range of about −30° C. to about 50° C at atmospheric pressure. A highly desirable propellant for use in connection with the subject composition is a mixture of dichlorodifluoromethane and dichlorotetrafluoroethane in a 25:75 blend.

The propellant will normally constitute from about 65 to 97 percent of the final composition, preferably from about 80 to 93 percent by weight thereof in an aerosol embodiment.

The antimicrobial composition will be employed in amounts of about 0.02 to 3.0%, preferably about 0.1 to 1.0% by weight of the total composition.

The following examples are further illustrative of the nature of the present invention and it is to be understood that the invention is not limited thereto. All amounts therein as well as in the appended claims are by weight unless otherwise indicated.

EXAMPLE 1

The antimicrobial combination is prepared by combining 2.70 parts of Ionene 10-10 Bromide with 10.00 parts SD 40 ethanol (95%), the resultant solution is then combined with the product resulting from the combination of 2.90 parts of Triclosan, 0.50 parts KOH and 15.0 parts SD 40 ethanol (95%). The foregoing is combined by the procedure as set forth in the specification.

EXAMPLE 2

The procedure of example 1 is followed with the exception that 2.36 parts of Ionene 10-10 chloride is employed in place of the Ionene 10-10 bromide and 0.40 parts NaOH is substituted for the KOH.

EXAMPLE 3

Ionene 10-10 Bromide, an aqueous solution, is treated with $Ag_2O$ suspension to yield insoluble AgBr and Ionene 10-10 Hydroxide, which can be separated from the AgBr by centrifugation or filtration. The Ionene Free Base can then be neutralized with a hydroalcoholic solution of Triclosan and a colloidal suspension of Triclosan/Ionene is obtained. This is then a useful form of the antimicrobial combination to be formulated into a roll-on lotion or deodorant cream. The latter should preferably be based upon nonionic emulsifiers.

In like manner, the various other anionic antimicrobial materials referred to earlier may be substituted for the Triclosan by merely employing that material in an amount equivalent to 1/100 of the molecular weight of that particular anionic component.

EXAMPLE 4

Aerosol Deodorant 0.1% to 0.5% Antimicrobial composition
9.5 Perfume
To 100% — Ethanol (anhydrous, denatured)
40.0% Propellant —12 (Fluorocarbon)

EXAMPLE 5

Deodorant/Antiperspirant

|  |  |
|---|---|
| 0.15% Antimicrobial composition | 48 parts Ionene 10—10 Br 52 parts Triclosan |
| 2.0% Al Chlorohydrate-Alcohol soluble complex | |
| 8.0% Ethanol | |
| 9.5 Perfume | |
| To 100% Fluorcarbon Propellant | |

EXAMPLES 6-10

These examples illustrate the preparation of a liquid product which may be employed in a roll-on applicator.

| Ingredients | 6 | 7 | 8 | 9 | 10 |
|---|---|---|---|---|---|
| Aluminum chlorhydroxide | 12.5 | 23 | 22 | 24 | 24 |
| Aluminum chloride hexahydrate | — | — | 1.0 | — | 1.5 |
| Antimicrobial composition | 0.1 | 0.3 | 0.5 | 1.0 | 2.0 |
| Ethyl alcohol | 17.5 | 17.5 | 17.5 | 17.5 | 17.5 |
| Surface-active agent | 1.0 | 1.0 | 1.0 | 1.0 | 1.0 |
| Gum | 0.65 | 0.65 | 0.65 | 0.65 | 0.65 |
| Allantoin | 0.1 | 0.1 | 0.1 | 0.1 | 0.1 |
| Glycerine | 3.0 | 3.0 | 3.0 | 3.0 | 3.0 |
| Water | Bal. | Bal. | Bal. | Bal. | Bal. |

The compositions are prepared by blending the ethyl alcohol (S.D. 40), perfume and surface-active agent (Igepal CO-630), aromatic polyethylene glycol ether, warming the mixture, and slowly adding the gum (hydroxypropyl methylcellulose) with stirring for a sufficient time to permit swelling of the gum to form a homogeneous solution. The major part of the water is then added and the remaining ingredients are added slowly in any desired order to the warmed solution with stirring. The amount of aluminum chlorhydroxide indicated is on a solids basis and it is added in the form of an approximately 50% aqueous solution to form a clear homogeneous liquid and the aluminum chloride is added in powder form.

EXAMPLE 11

A typical formulation for a cream is

| Ingredients: | Percent |
|---|---|
| Antimicrobial composition | 3 |
| Aluminum chlorhydroxide | 18 |
| Glyceryl monostearate | 11 | with the balance being primarily water, and small amounts of perfume, emollient materials, preservative, etc.

EXAMPLE 12

The following dry powder aerosol composition is prepared:

|  | % by weight |
|---|---|
| antimicrobial composition | 3.0 |
| aluminum basic chloride powder ($Al_2OH_5Cl$) | 3.0 |
| isopropyl palmitate | 0.5 |
| "Bentone 38" | 0.5 |
| propylene carbonate | 0.165 |
| propellant - dichlorodifluoromethane: dichlorotetrafluoroethane (25:75) | 92.835 |

The aerosol suspension is prepared by first making a suspension concentrate. The concentrate is prepared by blending the Bentone 38 with the isopropyl palmitate, the antimicrobial composition, and the propylene carbonate (wetting agent). The mixture is vigorously mixed at a temperature of about 20° C. to form a gel. The aluminum basic chloride is then added along with a portion of the propellant and the composition mixed to form a homogeneous concentrate mixture. The concentrate is then placed in a can, sealed with a suitable aerosol valve, and pressurized with the propellant. Finally, the aerosol container is shaken and a stable aerosol suspension thereby obtained.

EXAMPLE 13

The following composition is prepared in the same manner as the composition of the proceding EXAMPLE.

|  | % by weight |
|---|---|
| antimicrobial composition | 3.0 |
| aluminum basic chloride powder ($Al_2OH_5Cl$) | 3.5 |
| isopropyl palmitate | 1.5 |
| propylene carbonate | 0.06 |
| perfume | 0.1 |
| propellants-trichlorofluoromethane: dichlorodifluoromethane (65:35) | 92.84 |

EXAMPLE 14

The following composition is made in the same way as in the preceding EXAMPLE.

|  | % by weight |
|---|---|
| antimicrobial composition | 3.0 |
| aluminum basic chloride powder ($Al_2OH_5Cl$) | 3.0 |
| isopropyl palmitate | 0.5 |
| diisopropyl adipate | 0.5 |
| "Bentone 27" | 0.4 |
| propylene carbonate | 0.1 |
| perfume | 0.200 |
| propellant - dichlorodifluoromethane: trichloromonofluoromethane (35:65) | 92.3 |

In this composition, the vehicle constitutes a mixture of isopropyl palmitate and diisopropyl adipate.

EXAMPLE 15

The following composition is prepared:

| | % by weight |
|---|---|
| antimicrobial composition | 3.0 |
| aluminum chloride hexahydrate powder (AlCl$_3$ . 6H$_2$O) | 1.0 |
| aluminum chloride powder (Al$_2$Cl$_6$) | 1.0 |
| urea | 0.25 |
| "Bentone 34" | 0.35 |
| propylene carbonate | 0.1 |
| perfume | 0.200 |
| propellant (same as the preceding EXAMPLE) | 94.1 |

These compositions are highly effective in the reduction of perspiration and axillary odor, and for antibacterial activity. The use of these products results in considerable reduction in axillary odor and a relatively low bacterial count.

While there is shown and described a present preferred embodiment of the invention, it is to be understood that the invention is not limited thereto, but may be otherwise variously embodied and practiced within the scope of the following claims.

I claim:

1. An antimicrobial composition comprising the product resulting from admixing (1) a compound selected from the group consisting of a poly (quaternary ammonium) compound having the formula

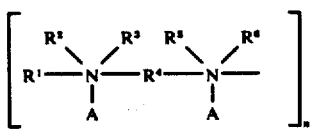

wherein $n$ is about 2–200, A is the anion of an acid, and R$^1$ and R$^4$ are polymethylene containing 6 to 20 carbon atoms and R$^2$, R$^3$, R$^5$ and R$^6$ are alkyl containing 1 to 3 carbon atoms

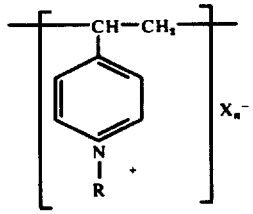

wherein $n = 10^2$ to $5\times10^3$; R is alkyl containing 6 to 15 carbon atoms, x is halide metho-sulfate or etho-sulfate and (2) at least one compound selected from the group consisting of compounds having the formula

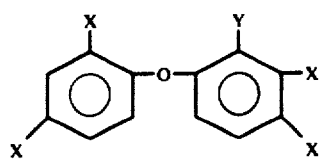

wherein Y is hydrogen or hydroxy and X halogen, —CF$_3$ or —H,

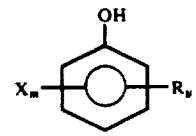

wherein R is a substituent selected from the group consisting of methyl and phenyl, each X is at least one of bromine and chlorine, y is 0 or 1, and m is an integer of about 1 to 5 (5-y), inclusive;

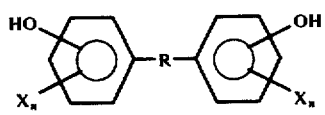

wherein X represents a halogen such as chlorine or bromine, $n$ represents an integer of about 1 to 3, and R represents S or a divalent alkylene radical having about 1 to 4 carbon atoms;

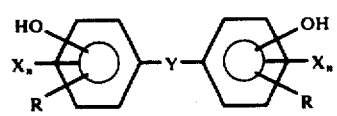

wherein X represents a halogen such as chlorine or bromine, $n$ is an integer of about 1 to 3, R is an alkyl group containing about 1 to 4 carbon atoms and Y is S or a divalent radical having about 1 to 4 carbon atoms;

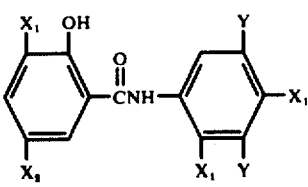

wherein each $X_1$ represents hydrogen or halogen, $X_2$ represents a halogen, and Y represents hydrogen, halogen or trifluoromethyl;

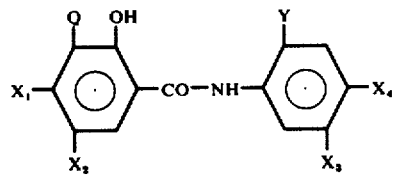

wherein Q represents a member selected from the group consisting of hydrogen, chlorine, bromine, and iodine, $X_1$ and $X_2$ each represent a member selected from the group consisting of hydrogen, chlorine, bromine, iodine and CH$_3$, $X_3$ represents a member selected from the group consisting of hydrogen, chlorine, bromine and CH$_3$ and $X_4$ and Y each represent a member selected from the group consisting of hydrogen, chlorine and bromine, there being at least two halogen substituents in the X positions;

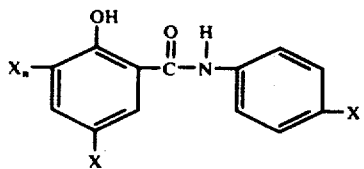

wherein X is chlorine, bromine or iodine and n is 0 to about 1;

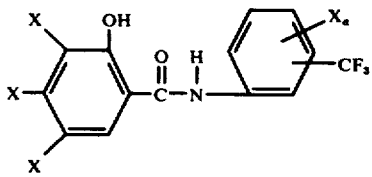

wherein X is chlorine, bromine, iodine or hydrogen and a is 0 to about 2, with the proviso that there is at least one and not more than three directly attached halogen atoms, none of which is adjacent to any of the others or to the CF$_3$ group.

2. A composition as defined in claim 1 wherein component (2) has the formula

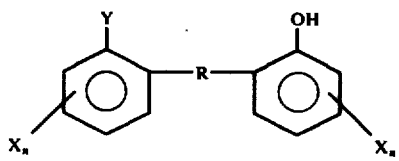

wherein R is —CH$_2$, S or O, X is halogen, n is about 1–3 and Y is H or —OH.

3. A composition as defined in claim 1 wherein component (2) is te formula VIII compound.

4. A composition as defined in claim 1 wherein component (2) is the formula IV compound.

5. A composition as defined in claim 1 wherein component (2) is the formula VI compound.

6. A composition as defined in claim 1 wherein about 1 mole of component (2) is employed for about each 1 equivalent of component (1).

7. A composition as defined in claim 1 wherein component (1) has a molecular weight of at about 5,000 to about 40,000.

8. A composition as defined in claim 1 wherein component (1) has repeating units of the formula:

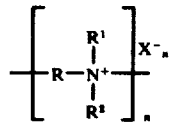

wherein R is a normal or branched chain alkylene group having about 6 to 16 carbon atoms, R$^1$ and R$^2$ is CH$_3$, C$_2$H$_5$, or C$_2$H$_4$OH, and X is R, Cl, Br, I, OSO$_3$CH$_3$, or CH$_3$COO.

9. A composition as defined in claim 8 wherein, in the formula for said repeating units, R is (CH$_2$)$_{10}$, R$^1$ and R$^2$ are each CH$_3$, and X is Br.

10. A deodorant composition comprising a liquid medium comprising at least one member selected from the group consisting of water, alcohol, and a liquified normally gaseous propellant and containing an antimicrobially effective amount ranging from about 0.02 to 3.05 by weight of a composition as defined in claim 1.

11. A deodorant composition as defined in claim 10 wherein said liquid medium contains water.

12. A deodorant composition as defined in claim 10 wherein said liquid medium contains alcohol.

13. A deodorant composition as defined in claim 10 wherein said liquid medium contains a liquified normally gaseous propellant.

14. A deodorant composition as defined in claim 10 wherein said liquid medium also contains about 0.5 to 15% by weight of a powdered astringent antisperspirant material selected from the group consisting of salts and complexes of zirconium, zinc, aluminum, and iron which are insoluble in alcohol and liquified normally gaseous propellants.

* * * * *